United States Patent [19]

Drivon et al.

[11] Patent Number: 5,545,776
[45] Date of Patent: Aug. 13, 1996

[54] SYNTHESIS OF N-PERFLUOROOCTYL BROMIDE

[75] Inventors: Gilles Drivon, Saint-Martin-En-Haut; Jacques Kervennal, Lyons, both of France

[73] Assignee: Elf Atochem S.A., Puteaux, France

[21] Appl. No.: 453,931

[22] Filed: May 30, 1995

Related U.S. Application Data

[63] Continuation of Ser. No. 257,217, Jun. 8, 1994, abandoned, which is a continuation of Ser. No. 986,392, Dec. 7, 1992, abandoned.

[30] Foreign Application Priority Data

Dec. 20, 1991 [FR] France .................. 91 15877

[51] Int. Cl.$^6$ .................................................. C07C 19/07
[52] U.S. Cl. ........................................................ 570/174
[58] Field of Search .............................................. 570/174

[56] References Cited

U.S. PATENT DOCUMENTS 3,456,024  7/1969  Loree .
5,057,633  10/1991  Drivon et al. .
5,073,651  12/1991  Raab .

FOREIGN PATENT DOCUMENTS 516572   9/1955  Canada .................. 570/174
0428039  5/1991  European Pat. Off. .
0429331  5/1991  European Pat. Off. .
1512068  2/1968  France .

OTHER PUBLICATIONS

McBee et al Indust & Eng Chem. vol. 39, No. 3, Mar. 1947, pp. 420, 421.

*Primary Examiner*—Alan Siegel
*Attorney, Agent, or Firm*—Spencer & Frank

[57] ABSTRACT

The invention relates to the preparation of n-perfluorooctyl bromide. The continuous process according to the invention consists in reacting bromine with 1-hydroheptadecafluoro-n-octane in the gaseous phase, at a temperature between 450° and 520° C. in a $Br_2/C_8F_{17}H$ mole ratio which can be from 0.2 to 5 and with a contact time between 2 and 240 seconds.

The $C_8F_{17}Br$ selectivity is almost complete and information of toxic sub-products like perfluoroisobutene is avoided.

8 Claims, No Drawings

SYNTHESIS OF N-PERFLUOROOCTYL BROMIDE

This is a continuation of application Ser. No. 08/257,217, filed on Jun. 8, 1994 now abandoned; which is a Continuation of Ser. No. 07/986,392, filed on Dec. 7, 1992, both abandoned.

FIELD OF THE INVENTION

The present invention relates to the field of perfluoroalkyl bromides and its subject is more particularly the preparation of n-perfluorooctyl bromide $C_8F_{17}Br$.

BACKGROUND OF THE INVENTION

This compound, also known by the abbreviation PFOB, is used in numerous fields, in particular in medicine as a radiopaque agent (contrast agent for X-rays) or as an oxygen carrier in blood substitutes.

In its Patent EP 0,298,870 and its Patent Application EP 90403118.4, the Applicant Company described processes for preparing perfluoroalkyl bromides $R_FBr$ (in particular PFOB) from the corresponding perfluoroalkanesulphonyl chlorides $R_FSO_2Cl$ which are reacted either with gaseous HBr in the presence of a catalyst (EP 0,298,870), or with a quaternary ammonium or phosphonium bromide (EP 90403118.4). The yields obtained are generally high, but the sulphonyl chloride $R_FSO_2Cl$ used is an advanced material since its synthesis from the corresponding iodide $R_FI$ requires two reaction stages according to the equation:

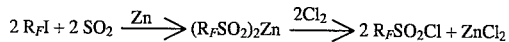

available in industrial quantities. Although this way is more direct, it has the drawback of leading to a product which still contains residual $R_FI$ which it is difficult to separate from the $R_FBr$ desired. This is more particularly the case for PFOB which must have a $C_8F_{17}I$ content less than 100 ppm for its medical applications.

A technique which has been known for a long time and is used industrially for preparation of trifluoromethyl bromide $CF_3Br$ consists in thermal bromination of trifluoromethane. In the absence of a catalyst, this reaction is generally carried out at temperatures from 600° to 700° C. so as to obtain a high conversion ratio.

The U.S. Pat. No. 3,456,024 relates to a process for preparation of perfluoroalkyl or perfluoroalkylene chlorides or bromides which consists in reacting, in a temperature range from 450° to 700° C., chlorine or bromine with various compounds containing a perfluoroalkyl $R_f$ or perfluoroalkylene $R'_f$ radical such as the compounds $R_fSF_5$, $R_fSO_2X$, $(R_fSO_2)_2O$, $HR'_fCH_2OH$, $R_fH$ and $R_f(CH_2CH_2)_nX'$, X designating a fluorine, chlorine or bromine atom or a hydroxyl group, X' a chlorine or bromine atom, and n a number from 1 to 5. In this Patent, bromination of a hydroperfluoroalkane $R_fH$ is only illustrated by a single example, namely Example 7 relating to the bromination of the compound n-$C_7F_{15}H$ with the following $C_7F_{15}Br$ yields by mole:

| Temperature (°C.) | Yield |
| --- | --- |
| 500 | 29% |
| 550 | 49.5% |
| 600 | 81.4% |

No mention is made of the selectivity of the reaction, which is a very important parameter for implementation of an industrial process.

Considering the high temperatures necessary to obtain industrially acceptable conversion ratios both in the bromination of trifluoromethane and in that of the compound n-$C_7F_{15}H$, the application of this technique to industrial preparation of PFOB for medical use from 1-hydroheptadecafluoro-n-octane ($C_8F_{17}H$) could not seriously be envisaged. In fact, this compound is thermally unstable and decomposes above 510° C. into toxic products, in particular perfluoroisobutene (PFIB) which is known for its extreme toxicity (see for example the articles by E. W. Cook and J. S. Pierce, Nature, 242, 1973, p. 5396–7 and by J. W. Clayton, Environmental Health Perspectives 21, 1977, pp. 255–267). Moreover, PFOB itself is thermally unstable above 520° C.

It has now been found that, in the particular case of the compound $C_8F_{17}H$ and its brominated derviative, a high yield for the reaction can be obtained while operating at temperautres lower than those taught by the prior technique.

The process according to the invention for continuous preparation of PFOB is characterised in that bromine is reacted in the gaseous phase with 1-hydroheptadecafluoro-n-octane in a $Br_2/C_8F_{17}H$ mole ratio between 0.2 and 5 (preferably between 0.5 and 2.5), at a temperature between 450° and 520° C. (preferably between 470° and 510° C.) and with a contact time between 2 and 240 seconds (preferably between 5 and 60 seconds).

This set of operating conditions leads to a high conversion ratio and a selectivity at least equal to 99%, without formation of toxic subproducts like PFIB. The unprocessed PFOB obtained is furthermore free from any trace (detection limit: ≦100ppm) of residual $C_8F_{17}I$ which might be contained in the starting $C_8F_{17}H$.

The process according to the invention can be implemented in any kind of reactor which is suitable for a gaseous phase reaction, in particular in a tubular reactor optionally fitted with packing in order to promote mixture of the gases. Equipment made of quartz or of glass is advantageously used, but any metallic material can also be used (for example Monel, Inconel and Hastelloy) which is capable of resisting the corrosive action of bromine and hydrobromic acid at the reaction temperature chosen.

Although it is not indispensable, the reaction of bromine with $C_8F_{17}H$ can be carried out in the presence of an inert gaseous diluent such as, for example, nitrogen or PFOB itself.

Industrially, it is preferred to work at atmospheric pressure, but working at a pressure greater than atmospheric pressure would not depart from the scope of the present invention, provided that the reaction system stayed in the gaseous state.

The gases leaving the reactor which contain the PFOB formed and the unconverted $C_8F_{17}H$, as well as the hydrobromic acid which is a sub-product of the reaction:

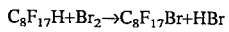

and possibly unreacted or excess bromine are cooled, then neutralized by an aqueous alkaline solution and/or reduced by an aqueous solution of sodium sulphite or metabisulphite. After pouring off the organic phase, the unconverted compound $C_8F_{17}H$ can, after separation by distillation, be recycled to the entry of the reactor.

In accordance with an advantageous method, the gases leaving the reactor can, before neutralization and/or reduction, be treated by chlorine so as to reoxidize the hydrobromic acid which is a sub-product into bromine which can thus be recycled in the process.

EXAMPLES

The following examples illustrate the invention without limiting it.

Example 1

Use is made of a quartz tubular reactor (internal diameter: 60 mm; height: 700 mm) uniformly heated over all its height and packed at the bottom over a height of 150 mm with quartz rings (diameter: 5 mm) in order to promote mixing of the gases.

The lower entry of the reactor is preceded by an evaporator into which are simultaneously and continuously introduced bromine at a flow rate of 320 g/h and $C_8F_{17}H$ at a flow rate of 420 g/h, that is to say a $Br_2/C_8F_{17}H$ mole ratio equal to 2/1 at the entry of the reactor.

The reaction temperature is fixed at 500° C. and the contact time of the reactants at 60 seconds.

On leaving the reactor, the products are cooled, reduced by a solution of sodium sulphite, then washed by a weakly alkaline solution. Chromatographic analysis in the gaseous phase indicates an overall conversion ratio ($TT_G$) of the $C_8F_{17}H$ equal to 83% and a $C_8F_{17}Br$ selectivity of 100%.

EXAMPLE 2 (comparative)

The procedure is as in Example 1 but at 550° C. instead of 500° C.

The overall conversion ratio of $C_8F_{17}H$ is higher (90.5%), but a very large drop in the $C_8F_{17}Br$ selectivity (82%) is observed.

EXAMPLES 3 to 10

The procedure is as in Example 1 but with different settings of the running parameters (reaction temperature, $Br_2/C_8F_{17}H$ mole ratio and contact time).

The operating conditions and the results obtained are collected in the following table.

| | OPERATING CONDITIONS | | | RESULTS | |
|---|---|---|---|---|---|
| EX-AMPLE | Temperature (°C.) | $Br_2/$ $C_8F_{17}H$ mole ratio | Contact time (s) | TTG (%) of $C_8F_{17}H$ | $C_8F_{17}Br$ selectivity |
| 3 | 450 | 1 | 30 | 21 | 100 |
| 4 | 500 | 1.02 | 30 | 59 | 99.8 |
| 5* | 550 | 0.99 | 30 | 72.5 | 87.5 |
| 6 | 500 | 2 | 30 | 71.5 | 99.7 |
| 7* | 550 | 2.03 | 30 | 90 | 92.3 |
| 8 | 500 | 0.96 | 60 | 66.5 | 99.1 |
| 9* | 550 | 1 | 60 | 74.5 | 78 |
| 10 | 525 | 1.5 | 45 | 85 | 97.0 |

*Comparative Example

A sharp drop in the selectivity is systematically noticed when the temperature goes from 500° to 550° C., whatever the mole ratio and/or the contact time used. This decrease in selectivity is detectable above 525° C. (Example 10) which gives good confirmation of the thermal instability of $C_8F_{17}H$ and $C_8F_{17}Br$ above 520° C.

We claim:

1. Continuous process for the selective preparation of n-perfluorooctyl bromide, comprising reacting bromine in the gaseous phase with 1-hydroheptadecafluoro-n-octane $C_8F_{17}H$ in a $Br_2/C_8F_{17}H$ mole ratio between 0.5 and 2.5, at a temperature between 470° and about 510° C., and with a contact time between 5 and 60 seconds.

2. Process according to claim 1 wherein the procedure is carried out in the presence of an inert diluent.

3. Process according to claim 1 wherein the procedure is carried out at atmospheric pressure.

4. Process according to claim 1, wherein the prepared n-perfluorooctyl bromide has $\leq 100$ ppm of $C_8F_{17}I$.

5. Process according to claim 1, wherein the prepared n-perfluorooctyl bromide has a purity suitable for medical use.

6. Process according to claim 1, wherein the prepared n-perfluorooctyl bromide is formed without toxic subproducts.

7. Process according to claim 6, wherein the prepared n-perfluorooctyl bromide is formed without perfluoroisobutene.

8. Continuous process for the selective preparation of n-perfluorooctyl bromide ($C_8G_{17}Br$) comprising reacting bromine ($Br_2$) in the gaseous phase with 1-hydroheptadecafluoro-n-octane ($C_8F_{17}H$) in a $Br_2/C_8F_{17}H$ mole ratio between 0.5 and 2.5, at a temperature between 470° and about 510° C., and with a contact time between 5 and 60 seconds, wherein $C_8F_{17}Br$ selectivity is at least 99% without formation of toxic subproducts, whereby the prepared $C_8F_{17}Br$ is suitable for medical use.

* * * * *